United States Patent
Nagamine et al.

(10) Patent No.: US 10,478,462 B2
(45) Date of Patent: Nov. 19, 2019

(54) ALCOHOL METABOLISM PROMOTER

(71) Applicant: NICHIREI BIOSCIENCES INC., Tokyo (JP)

(72) Inventors: Kenichi Nagamine, Tokyo (JP); Hideya Tanabe, Tokhyo (JP)

(73) Assignee: NICHIREI BIOSCIENCES INC., Tokyo (JP)

( * ) Notice: Subject to any disclaimer, the term of this patent is extended or adjusted under 35 U.S.C. 154(b) by 55 days.

(21) Appl. No.: 15/525,053

(22) PCT Filed: Nov. 6, 2015

(86) PCT No.: PCT/JP2015/081335
§ 371 (c)(1),
(2) Date: May 5, 2017

(87) PCT Pub. No.: WO2016/072496
PCT Pub. Date: May 12, 2016

(65) Prior Publication Data
US 2017/0319630 A1     Nov. 9, 2017

(30) Foreign Application Priority Data

Nov. 7, 2014   (JP) ................................ 2014-227387

(51) Int. Cl.
| | | |
|---|---|---|
| *A61K 31/716* | (2006.01) | |
| *A61K 35/618* | (2015.01) | |
| *A61K 9/00* | (2006.01) | |
| *A61K 31/715* | (2006.01) | |
| *A61K 45/00* | (2006.01) | |
| *A61P 39/00* | (2006.01) | |
| *A61P 39/02* | (2006.01) | |

(52) U.S. Cl.
CPC .......... *A61K 35/618* (2013.01); *A61K 9/0053* (2013.01); *A61K 31/715* (2013.01); *A61K 31/716* (2013.01); *A61K 45/00* (2013.01); *A61P 39/00* (2018.01); *A61P 39/02* (2018.01)

(58) Field of Classification Search
None
See application file for complete search history.

(56) References Cited

U.S. PATENT DOCUMENTS

| | | | | |
|---|---|---|---|---|
| 3,471,300 | A | * | 10/1969 | Wendt .................. A22C 29/043 426/407 |
| 2007/0207957 | A1 | | 9/2007 | Katayama et al. |
| 2009/0054351 | A1 | | 2/2009 | Matuschka-Greiffenclau |
| 2012/0220547 | A1 | * | 8/2012 | Russo ..................... A23L 33/10 514/54 |
| 2014/0105877 | A1 | | 4/2014 | Matuschka-Greiffenclau |

FOREIGN PATENT DOCUMENTS

| | | | |
|---|---|---|---|
| JP | 2005-261408 | A | 9/2005 |
| JP | 3793239 | B2 | 7/2006 |
| JP | 2007-210989 | A | 8/2007 |
| JP | 2007210989 | * | 8/2007 |
| JP | 2007-246478 | A | 9/2007 |
| JP | 2011-037790 | A | 2/2011 |
| JP | 2013-189437 | A | 9/2013 |
| KR | 10-2014-0074080 | A | 6/2014 |
| WO | 2005/102321 | A1 | 11/2005 |
| WO | 2014/172785 | A1 | 10/2014 |

OTHER PUBLICATIONS

Databese WPI, Week 199951, Thomson Scientific, London, GB; AN 1999-600150, XP002780830, 1pp.
Takeshi Chijimatsu et al., "Effect of Freshwater Clam(*Corbicula fluminea*) Extract on Liver Function in Rats", Nippon Shokuhin Kagaku Kogaku Kaishi, Feb. 2008, 63-68 pages, vol. 55, No. 2, Japan, 6pp.
Si-Kyung Kim et al., "Effects of Hot Water Extracts of Domestic Blue Mussel and New Zealand Green Lipped Mussel on Alcohol Metabolizing Enzymatic, DPPH Radical Scavenging, and Angiotensin Converting Enzyme Inhibitory Activities", Journal of the Korean Society of Food Science and Nutrition, Sep. 30, 2014, 1363-1368 pages, vol. 43, No. 9, Korea, 6pp.
Extended European Search Report in EP Application No. 15857073. 9, dated May 22, 2018, 9pp.
International Search Report in PCT/JP2015/081335, dated Jan. 12, 2016.
N. Rukma Reddy et al., Composition, Flavor Extract, Protease, and Glycosidases of Clam Bellies Collected from Clam Processing Plants, 1989, pp. 341-345, vol. 37 No. 2, Journal of Agricultural and Food Chemistry.

* cited by examiner

*Primary Examiner* — Traviss C McIntosh, III
(74) *Attorney, Agent, or Firm* — Hauptman Ham, LLP

(57) ABSTRACT

The present invention relates to an agent for effectively suppressing an increase in a blood acetaldehyde level. More specifically, the present invention relates to an alcohol metabolism promoter comprising glycogen obtained from a Veneroida bivalve.

4 Claims, 3 Drawing Sheets

ALCOHOL METABOLISM PROMOTER

CROSS-REFERENCE TO RELATED APPLICATIONS

This application is a National Phase of International Application Number PCT/JP2015/081335, filed Nov. 6, 2015. This application is also based upon and claims the benefit of priority of Japanese Patent Application No. 2014-227387, filed on Nov. 7, 2014, the entire contents of which are incorporated herein by reference.

TECHNICAL FIELD

The present invention relates to a novel alcohol metabolism promoter.

BACKGROUND ART

Acetaldehyde is an inevitable product in alcohol metabolism, but has a strong toxicity. It is generally known that acetaldehyde causes acute poisoning, gastrointestinal upset, nausea, headache, and an unpleasant symptom such as drink sickness or hangover when an alcohol drink is ingested excessively (Patent Literature 1).

When an alcohol is ingested excessively, alcohol metabolism is selectively enhanced in the liver. As a result, a large change may occur in a metabolism system of the liver. The majority of ingested alcohol becomes acetaldehyde through an alcohol dehydrogenase system present in cytosol of liver cells. Acetaldehyde is usually converted into acetic acid by being subjected to a dehydrogenation reaction by aldehyde dehydrogenase. However, when the alcohol ingestion amount is too large, or alcohol metabolism is late due to poor physical conditions, acetaldehyde is not fully processed, a blood acetaldehyde level is increased, and an unpleasant symptom such as drink sickness or hangover due to the toxicity of acetaldehyde may occur. Therefore, how to promote alcohol metabolism and suppress an increase in the blood acetaldehyde concentration is important for preventing an unpleasant symptom such as drink sickness or hangover.

In recent years, development of an oral agent for promoting alcohol metabolism and suppressing the blood acetaldehyde level at a low level has been studied (Patent Literature 2 and Patent Literature 3). However, still now, an oral agent capable of effectively promoting alcohol metabolism or suppressing an increase in the blood acetaldehyde level is required.

On the other hand, it has been reported that a processed shellfish food is used as a functional food having a health-promoting function. For example, it is known that a hepatic disorder is suppressed by suppressing an increase in AST and ALT values by using either a blue mussel molluscous portion or a blue mussel extract (Patent Literature 4).

However, there has been no report about a relationship between a Veneroida bivalve and an action for suppressing an increase in the blood acetaldehyde level.

This time, the present inventors administered an extract of a Veneroida bivalve comprising glycogen to a subject, and have found that an increase in the blood acetaldehyde level caused by ingestion of alcohol can be effectively suppressed. The present invention is based on this knowledge.

Therefore, an object of the present invention is to provide a novel alcohol metabolism promoter capable of suppressing an increase in the blood acetaldehyde level.

CITATION LIST

Patent Literature

Patent Literature 1: JP 3793239 B2
Patent Literature 2: JP 2013-189437 A
Patent Literature 3: JP 2007-246478 A
Patent Literature 4: JP 2011-37790 A

SUMMARY OF INVENTION

The present invention provides the following inventions.

(1) An alcohol metabolism promoter comprising glycogen.
(2) The alcohol metabolism promoter described in (1), in which the glycogen is derived from an extract of a Veneroida bivalve.
(3) The alcohol metabolism promoter described in (1) or (2), in which the bivalve is *Arctica islandica*.
(4) An alcohol metabolism promoter comprising an extract of a Veneroida bivalve.
(5) The alcohol metabolism promoter described in (4), in which the bivalve is *Arctica islandica*.
(6) The alcohol metabolism promoter described in any one of (1) to (5), in which the alcohol metabolism promoter is in a form of a single oral ingestion unit.
(7) The alcohol metabolism promoter described in any one of (1) to (6), in which the alcohol metabolism promoter is an agent for suppressing an increase in a blood acetaldehyde level.
(8) The alcohol metabolism promoter described in any one of (1) to (7), in which the alcohol metabolism promoter is an agent for preventing drink sickness or hangover.
(9) A method for suppressing an increase in a blood acetaldehyde level, including causing a subject in need thereof to ingest glycogen or an extract of a Veneroida bivalve in an effective amount.
(10) The method described in (9), in which the method is a method for promoting alcohol metabolism.
(11) The method described in (9) or (10), in which the method is a method for preventing drink sickness or hangover.
(12) Use of glycogen or an extract of a Veneroida bivalve in manufacturing an agent for suppressing an increase in a blood acetaldehyde level.
(13) The use described in (12), in which the agent is an alcohol metabolism promoter.
(14) The use described in (12) or (13), in which the agent is an agent for preventing drink sickness or hangover.
(15) Use of glycogen or an extract of a Veneroida bivalve as an agent for suppressing an Increase in a blood acetaldehyde level.

The present invention can effectively suppress an Increase in a blood acetaldehyde level in a subject who has ingested alcohol. The agent of the present invention is advantageous in preventing acute poisoning, gastrointestinal upset, nausea, vomiting, headache, heaviness of the head, feeling of fatigue, drowsiness, muscle pain, diarrhea, dizziness, upset feeling, and an unpleasant symptom such as drink sickness or hangover when an alcohol drink is ingested excessively.

DETAILED DESCRIPTION OF THE INVENTION

Alcohol Metabolism Promoter

Figure 1:
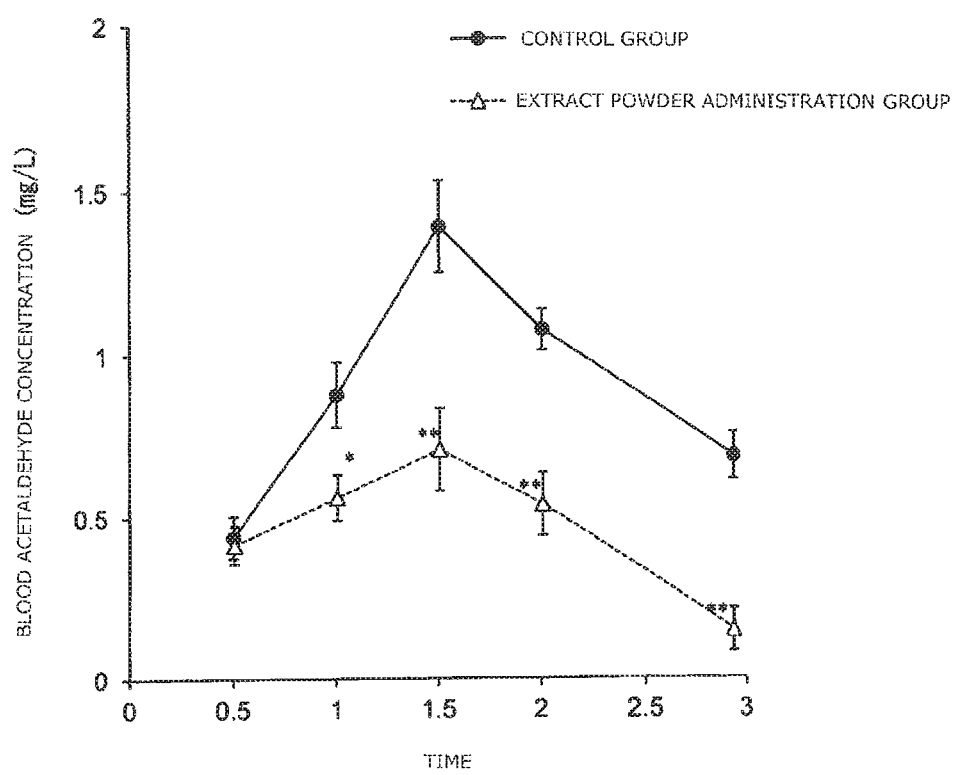
FIG. 1 is a graph illustrating a change in a blood acetaldehyde level of rats in a Veneroida bivalve extract powder administration group (repeated administration) and a control group (repeated administration).

One of characteristics of the alcohol metabolism promoter of the present invention is to comprise an extract of a Veneroida bivalve. It is a surprising fact that the extract of a Veneroida bivalve suppresses an increase in a blood acetaldehyde level significantly.

The kind of the Veneroida bivalve is not particularly limited as long as not interfering with an effect of the present invention. Examples thereof include *Fimbria soverbii, Tridacna gigas, Cardium costatum, Donax madagascariensis, Bassina disjecta, Lioconcha castrensis, Hysteroconcha lupanaria, Phylloda foliacea, Solen strictus, Panopea japonica,* and *Arctica islandica. Arctica islandica* is preferable. *Arctica islandica* is a bivalve usually having a size of about 3 to 5 inches, also referred to as Ocean (Quahog) Clam. It is known that *Arctica islandica* can be collected in a sea area having a depth of 120 to 200 feet in the East Coast of the United States.

The extract of the Veneroida bivalve in the present invention may be manufactured from a natural product, or a commercially available product may be used therefor. Examples of the commercially available product include SW Ocean Clam Juice (CODE 0431) and ESF Ocean Clam Juice (CODE 04ES) manufactured by Sea Watch International Ltd. in the United States.

The extract in the present invention is not particularly limited as long as not interfering with an effect of the present invention. However, an extract of a Veneroida bivalve with an aqueous medium (ethanol, water, a mixture thereof, or the like) is preferable, and an extract thereof with water is more preferable.

The extract in the present invention is not particularly limited as long as not interfering with an effect of the present invention, and may comprise water, a protein, a lipid, ash (mineral: sodium or the like), or a carbohydrate (glucose, mucopolysaccharide, glycogen, nucleic acid (DNA, RNA, or the like), or the like), for example. The contents of these components are not particularly limited. However, for example, in terms of a dry matter, the content of water may be from 0 to 10% by mass, the content of a protein may be from 0 to 30% by mass, the content of a lipid may be from 0 to 5% by mass, the content of ash may be from 0 to 5% by mass, and the content of a carbohydrate may be from 50 to 90% by mass. These contents can be determined by drying and measuring methods described in Example 1.

The extract of the present invention preferably comprises glycogen. The content of glycogen is not particularly limited as long as not interfering with an effect of the present invention. However, for example, the content may be 80% by mass or more, and is preferably from 50 to 90% by mass.

A molecular weight of glycogen in the present invention is not particularly limited as long as not Interfering with an effect of the present invention. However, the molecular weight is preferably 10000 or more, and more preferably 100000 or more. A molecular weight of a shellfish extract in the present Invention is not particularly limited as long as not interfering with an effect of the present invention. However, the molecular weight is preferably 10000 or more, and more preferably 100000 or more. Each of glycogen and the shellfish extract having the above molecular weight can be fractionated and concentrated in accordance with an ultrafiltration treatment described in Example 1.

A method for manufacturing an extract in the present invention is not particularly limited as long as not interfering with an effect of the present invention. For example, an extract of a Veneroida bivalve with an aqueous medium may be used directly. Alternatively, an extract may be obtained by compressing, grinding, or boiling a Veneroida bivalve as desired, collecting and concentrating an extract generated when an edible portion is separated from a body of the Veneroida bivalve, and extracting the extract with an aqueous medium. In addition, in the method for manufacturing an extract in the present invention, a purification treatment, a concentration treatment, a sterilization treatment, or the like using a known method may be performed as desired. Examples of the purification treatment include a protease treatment, a lipolytic enzyme treatment, a filtration treatment, an activated carbon treatment, a dialysis treatment (electrodialysis, or the like), and a centrifugal separation treatment. Examples of the concentration treatment include an ultrafiltration treatment and a freeze-drying treatment. The purification treatment is preferable for decomposing and removing a component other than glycogen in a bivalve, concentrating an extract, and increasing a glycogen concentration. The above treatments may be performed at any stage in the method for manufacturing an extract as long as not interfering with an effect of the present invention.

The extract in the present invention may be in any form of a solid, a powder, a granule, a liquid, and a slurry.

When the extract in the present invention is prepared into a powder or solid shape, for example, the extract can be solidified or powdered by a freeze-drying method or a spray drying method.

The extract in the present invention may be formed directly into a dosage form for promoting alcohol metabolism, suppressing an increase in a blood acetaldehyde level, or preventing drink sickness or hangover. Alternatively, a dosage form may be formed by mixing the extract in the present invention with an acceptable component in view of pharmacology or oral ingestion, such as an excipient, a binder, a preservative, a stabilizer, a flavor, or a liquid medium.

The dosage form in the present invention is not particularly limited, but examples thereof include a tablet, a granule, a capsule, and a drink.

The agent of the present invention is preferably formed of a single oral ingestion unit such that the amount thereof is an effective amount for suppressing an increase in the blood acetaldehyde level. The unit in the agent of the present invention may comprise glycogen in an amount of preferably 4 mg or more, more preferably 8 mg or more in terms of a dry mass as a single oral ingestion. When the agent of the present invention comprises glycogen in an amount of 80% by mass or more, an adult preferably ingests the agent of the present invention in an amount of 5 to 5000 mg, preferably of 10 to 2000 mg per day in a single dose or continuously.

In addition, the agent of the present invention is preferably provided in a form in which a single oral ingestion unit is packaged. Examples of a unit-packaged form of a single oral ingestion include a form to define a fixed amount by a pack, a container, or the like. On a surface thereof, components of a single oral ingestion or applications such as promoting alcohol metabolism, suppressing an increase in the blood acetaldehyde level, and preventing drink sickness or hangover may be displayed. Suitable examples of such a unit-packaged form include a supplement and a pharmaceutical preparation.

According to the agent of the present invention, an increase in the blood acetaldehyde level in a subject who has ingested alcohol can be effectively suppressed, alcohol metabolism can be promoted, and drink sickness or hangover can be prevented effectively. Therefore, according to an aspect of the present invention, use of glycogen or an extract of a Veneroida bivalve is provided in manufacturing an alcohol metabolism promoter. According to another aspect, use of glycogen or an extract of a Veneroida bivalve is provided in manufacturing an agent for suppressing an increase in the blood acetaldehyde level. According to still another aspect, use of glycogen or an extract of a Veneroida bivalve is provided in manufacturing an agent for preventing drink sickness or hangover.

A plan for administering the agent of the present invention can be set appropriately by a person skilled in the art depending on the age, the sex, and the condition of a subject as long as not interfering with an effect of the present invention. The agent of the present Invention may be administered to a subject continuously or in a single dose. According to a preferable aspect, the agent of the present invention is preferably administered to a subject in an amount of a single oral ingestion unit at least once before ingestion of alcohol, during ingestion thereof, or after ingestion thereof.

According to another aspect of the present invention, a method for preventing drink sickness or hangover, including causing a subject in need thereof to ingest the agent of the present invention in an effective amount for suppressing an increase in the blood acetaldehyde level is provided. According to an aspect of the present invention, the method for preventing drink sickness or hangover excludes a medical practice to a human. The method for preventing drink sickness or hangover in the present invention is preferably a method for promoting alcohol metabolism, and is more preferably a method for suppressing an increase in the blood acetaldehyde level. Here, the "effective amount for suppressing an increase in the blood acetaldehyde level" can be formed of the above single oral ingestion unit. In addition, "preventing" includes not only treating an established disease state or symptom but also preventing a disease state or symptom which may be established in the future.

A subject is a mammal, for example, a rodent, a dog, a cat, cattle, or a primate, and is preferably a human, and more preferably a human before ingestion of alcohol, during ingestion thereof, or after ingestion thereof. The subject may be a healthy person or a sick person, but is preferably a healthy person before ingestion of alcohol, during ingestion thereof, or after ingestion thereof. Examples of the healthy person include a person classified into "A" or "B" ("no abnormality" or "mild abnormality") as a result of a liver function item of a blood test based on the determination division of Japan Society of Ningen Dock (revised on Apr. 1, 2014). According to the above determination division of Japan Society of Ningen Dock, as a blood liver function parameter of a healthy person, an AST (GOT) value is 35 U/L or less, an ALT (GPT) value is 40 U/L or less, and a γ-GTP value satisfies a range of 80 U/L or less.

EXAMPLES

Hereinafter, the present invention will be described more specifically with reference to Examples. However, the technical scope of the present invention is not limited to these examples. Note that all the percentages and ratios used in the present invention are based on a mass unless otherwise indicated. In addition, unless otherwise indicated, units and measuring methods described herein are according to Japanese Industrial Standard (JIS standard).

Example 1

Manufacturing Extract of Veneroida Bivalve

To 2200 g of a Veneroida bivalve concentrate (Ocean Clam Concentrate/Sea Watch International, Ltd., place at which Veneroida bivalve was collected: sea area 3 to 200 miles off the Virginian coast in Massachusetts in the United States), 8800 g of purified water equivalent to four times the concentrate was added to obtain a diluted solution. Subsequently, protease (1.76 g of protease P "Amano" 3SD manufactured by Amano Enzyme Inc.) and peptidase (1.76 g of peptidase R manufactured by Amano Enzyme Inc.) which are respectively equivalent to 0.08% of the concentrated solution of a Veneroida bivalve were added thereto, and were stirred at 35° C. for five hours for enzymolysis. Subsequently, the resulting enzyme-treated solution was heated at 75° C. for two hours for enzyme deactivation and sterilization, and was allowed to cool. 10925 g of the resulting solution was subjected to centrifugation (4200 rpm/10 min, himacCR7 manufactured by Hitachi Koki Co., Ltd.), 10566 g of the separated supernatant was filtered (POLYSEP II 10 manufactured by Merck KGaA, 1.2 μm) to obtain 10344 g of a filtrate. In addition, the resulting filtrate was subjected to an ultrafiltration treatment (SARTOCON Slice Cassette Hydrosart 100K manufactured by Sartorius Stedim Japan K.K.), and was concentrated to 1794 g. Note that in the concentration step, an operation of adding water to the filtrate for concentration was repeated twice for desalting and purification. The concentrated solution was spray-dried using a spray dryer (L-8i type/atomizer manufactured by Ohkawara Kakohki Co, Ltd., 25000 rpm, 170° C.-85° C.), and 193 g of an extract powder of a Veneroida bivalve was obtained. Component analysis of the extract powder of the Veneroida bivalve was performed as follows.

Component Analysis
water: 7.3 g/100 g (105° C./3 hr drying)
protein: 1.6 g/100 g (Kjeldahl method)
lipid: 0.2 g/100 g (Soxhlet extraction method)
ash: 0.6 g/100 g (direct ashing method)
carbohydrate: 93.3 g/100 g (calculation formula: 100−(water+protein+lipid+ash)
sodium: 163 mg/100 g (atomic absorption spectrophotometry)
glycogen: 79.6 g/100 g (Somogyi modification method)
glucose: 90.1 g/100 g (high-performance liquid chromatographic method)
mucopolysaccharide: 0.4 g/100 g (carbazole-sulfuric acid method)
DNA: 0.12 g/100 g (high-performance liquid chromatographic method)
RNA: 0.04 g/100 g (high-performance liquid chromatographic method)
heavy metal (as Pb): not detected (sodium sulfide colorimeteric method/quantitive lower limit: 1 ppm)
number of general bacteria (number of living bacteria): $5.4 \times 10^3$/g (standard agar plate culture method)
coliform group: negative/2.22 g (BGLB method)

Example 2

Study of Action for Suppressing Increase in Blood Acetaldehyde Level by Repeated Oral Administration of Extract Powder of Veneroida Bivalve SD rats (7-week-old, male, obtained from Japan Charles River Co., Ltd.) were subjected to pre-breeding for eight days, and then were divided into two groups (n=6) of a Veneroida bivalve extract powder administration group and a control group for breeding (seven days). In the extract powder administration group, a solution having the extract powder dissolved at a concentration of 50 mg/mL in injection water (Fuso Pharmaceutical Industries, Ltd.) was orally administered in an amount of 10 mL/kg once daily (dose: 500 mg/kg). In the control group, injection water was administered in an amount of 10 mL/kg once daily. One hour after termination of oral administration for 7 days, a 25% ethanol/saline solution was administered into the tail vein such that the ethanol dose was 1 g/kg. 0.5, 1.0, 1.5, 2.0, and 3.0 hours after administration of ethanol, about 0.5 mL of blood was collected from the jugular vein in the absence of anesthesia using a disposable syringe including heparin sodium (Novo Heparin 10000 units, Mochida Pharmaceutical Co., Ltd.) and a needle. The obtained blood was mixed with 1 mol/L ice-cooled perchloric acid in an equal amount, and a supernatant was collected by centrifugation of 12,000 g×3 minutes at 4° C. The resulting supernatant was divided into a sample for blood ethanol concentration measurement and a sample for blood acetaldehyde level measurement, and were stored at −80° C. until the time of measurement. Blood ethanol concentration measurement was performed using an F kit ethanol (J.K International Inc.), and blood acetaldehyde level measurement was performed using an F kit acetaldehyde (J.K International Inc.). In a statistical test of measurement results, a test of homoscedasticity in the groups was performed by an F-test. In a case of homoscedasticity, inter-group comparison was performed by a Student-t test. In a case of heteroscedasticity, inter-group comparison was performed by an Aspin-Welch approximation test.

As illustrated in FIG. 1, in the Veneroida bivalve extract powder administration group, an increase in the blood acetaldehyde level (average±standard error) was significantly suppressed as compared to the control group (Student-t test, *: $p<0.05$, **: $p<0.01$ vs control group).

Example 3

Study of Action for Suppressing Increase in Blood Acetaldehyde Level by Single Oral Administration of Extract Powder of Veneroida Bivalve SD rats (7-week-old, male, obtained from Japan Charles River Co., Ltd.) were subjected to pre-breeding for eight days, and then were divided into two groups (n=6) of a Veneroida bivalve extract powder administration group and a control group for breeding (one day). In the extract powder administration group, a solution having the extract powder dissolved at a concentration of 50 mg/mL in injection water (Fuso Pharmaceutical Industries, Ltd.) was orally administered in an amount of 10 mL/kg once daily (dose: 500 mg/kg). In the control group, injection water was administered in an amount of 10 mL/kg once daily. One hour after termination of oral administration, a 25% ethanol/saline solution was administered into the tail vein such that the ethanol dose was 1 g/kg. 0.5, 1.0, 1.5, 2.0, and 3.0 hours after administration of ethanol, about 0.5 mL of blood was collected from the jugular vein in the absence of anesthesia using a disposable syringe including heparin sodium (Novo Heparin 10000 units, Mochida Pharmaceutical Co., Ltd.) and a needle. The obtained blood was mixed with 1 mol/L ice-cooled perchloric acid in an equal amount, and a supernatant was collected by centrifugation of 12,000 g×3 minutes at 4° C. The resulting supernatant was divided into a sample for blood ethanol concentration measurement and a sample for blood acetaldehyde level measurement, and were stored at −80° C. until the time of measurement. Blood ethanol concentration measurement was performed using an F kit ethanol (J.K International Inc.), and blood acetaldehyde level measurement was performed using an F kit acetaldehyde (J.K International Inc.). In a statistical test of measurement results, a test of homoscedasticity in the groups was performed by an F-test. In a case of homoscedasticity, inter-group comparison was performed by a Student-t test. In a case of heteroscedasticity, inter-group comparison was performed by an Aspin-Welch approximation test.

Figure 2:
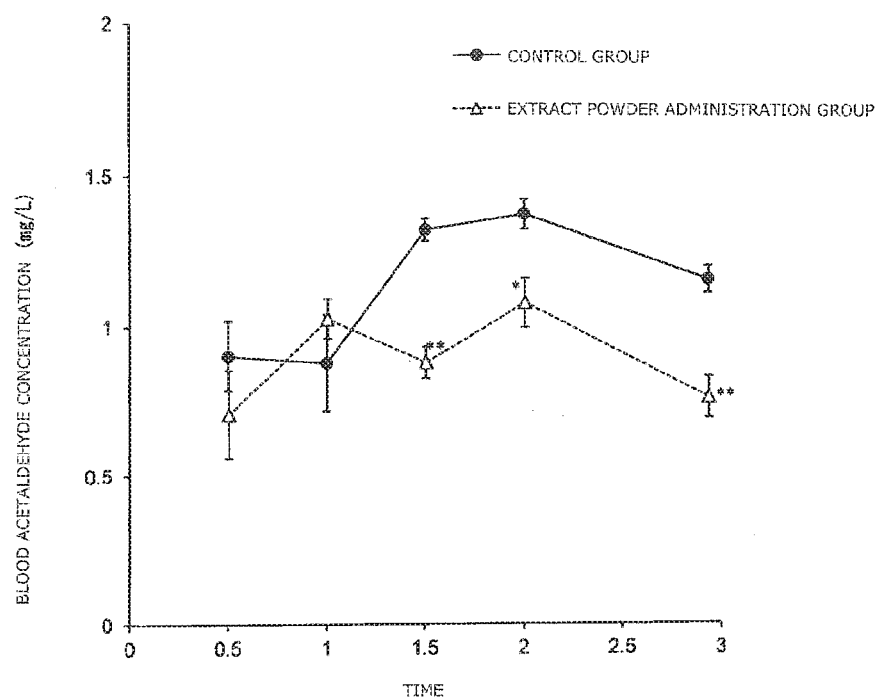
FIG. 2 is a graph illustrating a change in a blood acetaldehyde level of rats in a Veneroida bivalve extract powder administration group (single administration) and a control group (single administration).

As illustrated in FIG. 2, in the Veneroida bivalve extract powder administration group, an increase in the blood acetaldehyde level (average±standard error) was significantly suppressed as compared to the control group (Student-t test, *: $p<0.05$, **: $p<0.01$ vs control group).

Example 4

Study of Action for Suppressing Increase in Plasma Acetaldehyde Concentration by Repeated Oral Administration of Extract Powder of Veneroida Bivalve or Glucose SD rats (7-week-old, male, obtained from Japan Charles River Co., Ltd.) were subjected to pre-breeding for eight days, and then were divided into three groups (n=6) of a Veneroida bivalve extract powder administration group, a glucose administration group, and a control group for breeding (seven days). In the Veneroida bivalve extract powder administration group, a solution having the extract powder dissolved at a concentration of 50 mg/mL in injection water (Fuso Pharmaceutical Industries, Ltd.) was orally administered in an amount of 10 mL/kg once daily (dose: 500 mg/kg). In the glucose administration group, a glucose aqueous solution (Japanese Pharmacopoeia glucose injection solution, glucose concentration: 5%, manufactured by Otsuka Pharmaceutical Co., Ltd.) was orally administered once daily (dose: 500 mg/kg). In the control group, injection water was administered in an amount of 10 mL/kg once daily. One hour after termination of oral administration for 7 days, a 25% ethanol/saline solution was administered into the tail vein such that the ethanol dose was 1 g/kg. 0.5, 2.0, and 4.0 hours after administration of ethanol, about 1.0 mL of blood was collected from the jugular vein in the absence of anesthesia using a disposable syringe including heparin sodium (Novo Heparin 10000 units, Mochida Pharmaceutical Co., Ltd.) and a needle. The obtained blood was subjected to centrifugation (1800 g, 4° C., 15 minutes), and the plasma was separated and was frozen and stored at −80° C. To the plasma obtained by freezing and thawing, 1 mol/L perchloric acid in an equal amount was added and mixed therewith. Centrifugation was performed. A supernatant was collected and was neutralized with 0.7 mol/L trisodium phosphate in a half amount. The resulting product was used as a sample for plasma acetaldehyde concentration measurement. Plasma acetaldehyde concentration measurement was performed using an F kit acetaldehyde (J.K International Inc.). In a statistical test of measurement results, a test of homoscedasticity in the groups was performed by an F-test. In a case of homoscedasticity, inter-group comparison was performed by a Student-t test. In a case of heteroscedasticity, inter-group comparison was performed by an Aspin-Welch approximation test.

Figure 3:
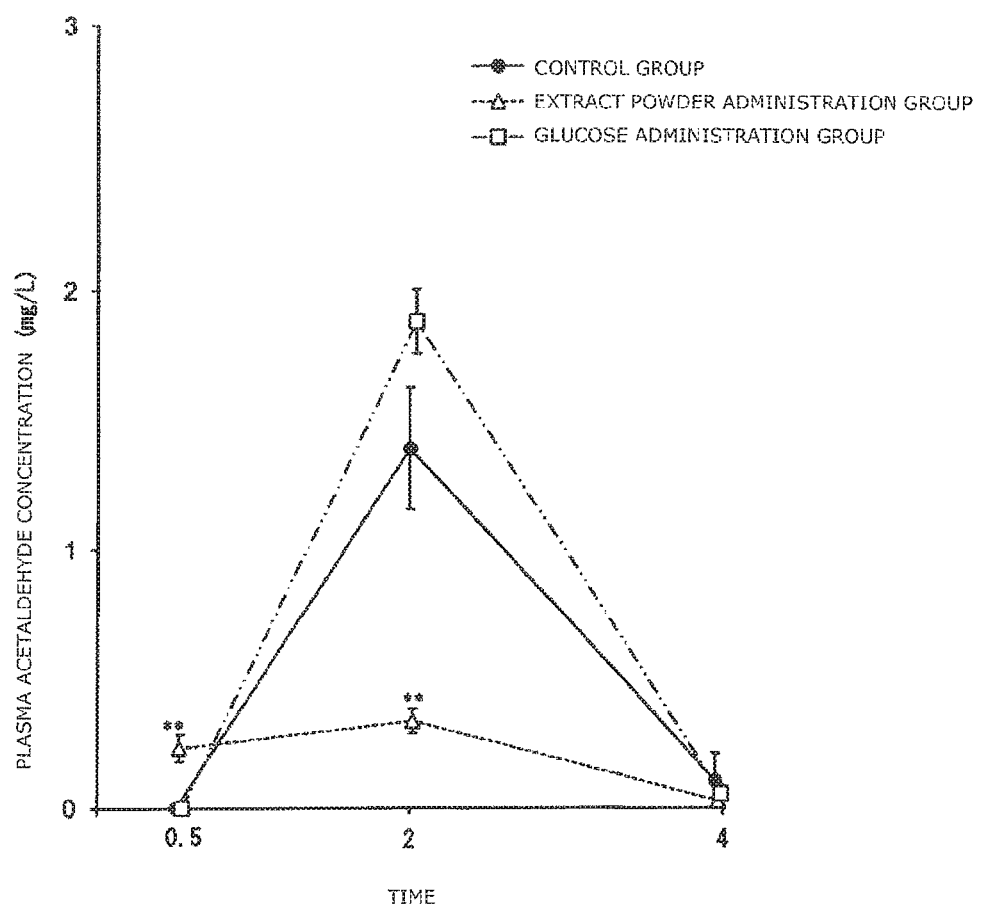
FIG. 3 is a graph illustrating a change in a plasma acetaldehyde concentration of rats in a Veneroida bivalve extract powder administration group (repeated administration), a glucose administration group (repeated administration), and control group (repeated administration).

FIG. 3 illustrates a result of the plasma acetaldehyde concentration measurement.

In the Veneroida bivalve extract powder administration group, an increase in the plasma acetaldehyde concentration (average±standard error) was significantly suppressed as compared to the control group and the glucose administration group (Aspin-Welch approximation test, *: $p<0.05$, **: $p<0.01$ vs control group).

When a Veneroida bivalve extract powder was subjected to acid hydrolysis, about 90% of decomposed products thereof was glucose in Example 1. This is because the Veneroida bivalve extract powder comprises glycogen which is a polymer of glucose as a main component. From a result of Example 4, it has been confirmed that an effect of suppressing an increase in the plasma acetaldehyde concentration in the Veneroida bivalve extract powder is not caused by glucose obtained by decomposing the Veneroida bivalve extract powder.

Example 5

Study of Action for Preventing Drink Sickness or Hangover by Veneroida Bivalve Extract Powder As subjects, 11 healthy persons (nine males, two females, age of 23 to 55) were selected. According to the determination division of Japan Society of Ningen Dock (revised on Apr. 1, 2014), all the subjects were classified into "A" or "B" in a liver function item of a blood test.

In order to start a test, as a test sample, three gelatin capsules filled with an extract powder of a Veneroida bivalve so as to be 1000 mg in total were prepared. The three capsules (1000 mg) were put Into a pouch on which the number (random number) and the test date were described.

As a placebo sample, three gelatin capsules filled with dextrin (Pinedex #2, derived from tapioca, manufactured by Matsutani Chemical Industry, Ltd.) so as to be 1000 mg in total were prepared. The three capsules (1000 mg) were put into a pouch on which the number (random number) and the test date were described Subsequently, the bag including the test sample and the bag including the placebo sample were put into one aluminum bag.

Note that the test date for the first term was described on one of the pouches in the aluminum bag, and the test date for the second term was described on the other pouch in order to perform a double blind test constituted by two terms. This is because adjustment is performed such that a subject ingests the test sample in one of the two terms and ingests the placebo sample in the other term. The number of subjects in each group in each term was five or six. Adjustment was performed in advance such that the number of subjects in each group in total of the two terms was the same.

In the first term of the test, a subject selected a sample from the aluminum bag according to the test date described on the pouch, and ingested the sample along with 100 mL of drinking water. Immediately after ingesting the sample, each subject Ingested alcohol in an amount slightly larger than the normally drinking amount (28 to 143 g, average 94 g) over two to three hours while taking the same meal as the other subjects.

In the next morning about 10 hours after termination of the alcohol ingestion, each subject performed a four-stage evaluation based on the following scores regarding subjective symptoms of "gastric upset", "nausea and vomiting", "headache and heaviness of the head," "feeling of fatigue", "drowsiness", "muscle pain", "Intestine (diarrhea)" and "dizziness and upset feeling".

4 points: having significantly
3 points: having slightly
2 points: hardly having
1 point: never having One week after the test day in the first term (after wash out), the test in the second term was performed. Specifically, the subject ingested the sample in the other pouch remaining in the same aluminum bag as in the first term along with 100 mL of drinking water. Here, guidance to ingest the meal and alcohol in the same content and the same amount as in the first term immediately after ingestion of the sample was given to the subject in advance.

About 10 hours after termination of the alcohol ingestion, each subject evaluated the subjective symptoms as in the first term.

From the test results of the above two terms, verification of an action for preventing drink sickness or hangover was performed.

Verification was performed for seven subjects who observed ingestion of alcohol in the same content and the same amount in the first term and the second term (six males and one female: alcohol ingestion amount: 42 to 143 g, average: 100 g). By separating the case of ingesting the test sample and the case of ingesting the placebo sample from each other, an average score in each evaluation item was calculated.

Table 1 indicates a result thereof.

TABLE 1

| Item | Extract of Veneroida bivalve | Placebo |
| --- | --- | --- |
| Gastric upset | 1.9 | 3.1 |
| Nausea and vomiting | 1.7 | 2.1 |
| Headache and heaviness of the head | 2.1 | 2.4 |
| Feeling of fatigue | 2 | 2.7 |
| Drowsiness | 1.9 | 2.4 |
| Muscle pain | 1.6 | 1.7 |
| Intestine (diarrhea) | 1.3 | 2 |
| Dizziness and upset feeling | 1.3 | 1.7 |

(Average value)

In all the evaluation items, it was confirmed that an average score value of the Veneroida bivalve extract administration group was lower than that of the placebo administration group and that there was a significant difference (Paired-t test, $p<0.05$) particularly in "gastric upset" and "feeling of fatigue".

When a total of the scores in all the evaluation items was calculated for each subject, four subjects indicated a score value two points or more lower in a case where the extract of the Veneroida bivalve was ingested than in a case where the placebo was ingested. This result also suggested effectiveness of ingestion of the extract of the Veneroida bivalve for relieving drink sickness or hangover.

Note that in the second term, four subjects could not ingest alcohol in the same content and the same amount as in the first term. Three of the four subjects ingested the placebo in the second term. It can be said that the three subjects ingested alcohol more easily in the first term in which the extract of the Veneroida bivalve was ingested than in the second term in which the placebo was ingested. It is considered that this result also suggests that ingestion of the extract of the Veneroida bivalve has an influence on promotion of alcohol metabolism.

The invention claimed is:

1. A method for suppressing an increase in a blood acetaldehyde level, comprising:
   causing a subject in need thereof to ingest an extract of a Veneroida bivalve in an effective amount, wherein an amount of glycogen in the extract is 50% to 90% by mass.

2. The method according to claim 1, wherein the method is a method for promoting alcohol metabolism.

3. The method according to claim 1, wherein the method is a method for preventing drink sickness or hangover.

4. The method according to claim 1, wherein the bivalve is *Arctica islandica*.

* * * * *